(12) United States Patent
Shida

(10) Patent No.: US 10,772,374 B2
(45) Date of Patent: Sep. 15, 2020

(54) LENS UNIT ATTACHMENT MECHANISM

(71) Applicant: SHOEI CO., LTD., Tokyo (JP)

(72) Inventor: Masayuki Shida, Tokyo (JP)

(73) Assignee: SHOEI CO., LTD., Tokyo (JP)

( * ) Notice: Subject to any disclaimer, the term of this patent is extended or adjusted under 35 U.S.C. 154(b) by 73 days.

(21) Appl. No.: 16/306,915

(22) PCT Filed: Apr. 5, 2017

(86) PCT No.: PCT/JP2017/014252
§ 371 (c)(1),
(2) Date: Dec. 4, 2018

(87) PCT Pub. No.: WO2017/212767
PCT Pub. Date: Dec. 14, 2017

(65) Prior Publication Data
US 2019/0133236 A1 May 9, 2019

(30) Foreign Application Priority Data

Jun. 8, 2016 (JP) .................. 2016-114206

(51) Int. Cl.
| | |
|---|---|
| *A42B 3/18* | (2006.01) |
| *G02C 3/00* | (2006.01) |
| *A42B 3/04* | (2006.01) |
| *A61F 9/02* | (2006.01) |
| *G02C 5/20* | (2006.01) |

(Continued)

(52) U.S. Cl.
CPC .............. *A42B 3/185* (2013.01); *A42B 3/04* (2013.01); *A61F 9/02* (2013.01); *G02B 7/023* (2013.01); *G02B 27/0176* (2013.01); *G02C 3/00* (2013.01); *G02C 5/20* (2013.01); *G02B 2027/0154* (2013.01); *G02B 2027/0169* (2013.01); *G02B 2027/0178* (2013.01)

(58) Field of Classification Search
CPC .. A42B 3/185; A42B 3/04; A42B 3/22; A61F 9/02; A61F 9/00; G02B 7/023; G02B 27/0176; G02C 3/00; G02C 5/20
USPC ........................................................ 359/815
See application file for complete search history.

(56) References Cited

U.S. PATENT DOCUMENTS

| | | | |
|---|---|---|---|
| 4,544,245 | A | 10/1985 | Stansbury, Jr. |
| 5,052,054 | A | 10/1991 | Birum |

(Continued)

FOREIGN PATENT DOCUMENTS

| | | |
|---|---|---|
| JP | H0312218 U | 2/1991 |
| JP | H04127221 U | 11/1992 |

(Continued)

*Primary Examiner* — James R Greece
(74) *Attorney, Agent, or Firm* — Thomas|Horstemeyer, LLP

(57) ABSTRACT

A good fitting sensation of a lens unit is obtained by performing fine adjustment of the position and angle of the lens unit. A lens unit attachment mechanism includes a frame member supporting a pair of lenses, side frame members extending rearward of the lenses from left and right end portions of the frame member, an angle adjustment member coupled to the lens unit and having two rotation pivot points, and a position adjustment retention member retaining the angle adjustment member so as to allow extending and retracting. The lens unit attachment mechanism adjusts the position and angle of the lens unit flexibly.

4 Claims, 8 Drawing Sheets

(51) Int. Cl.
*G02B 7/02* (2006.01)
*G02B 27/01* (2006.01)

(56) References Cited

U.S. PATENT DOCUMENTS

| | | | | |
|---|---|---|---|---|
| 5,230,101 A | * | 7/1993 | Hedges | A42B 3/226 |
| | | | | 2/10 |
| 6,892,393 B1 | | 5/2005 | Provost et al. | |
| 2003/0071961 A1 | | 4/2003 | Schubert | |
| 2010/0132085 A1 | * | 6/2010 | Beaudet | A42B 3/228 |
| | | | | 2/6.5 |

FOREIGN PATENT DOCUMENTS

| | | |
|---|---|---|
| JP | H07279939 A | 10/1995 |
| JP | H11346336 A | 12/1999 |
| JP | 2000178820 A | 6/2000 |
| JP | 2000303244 A | 10/2000 |
| JP | 2005061449 A | 3/2005 |
| JP | 2005309272 A | 11/2005 |
| WO | 2015059014 A1 | 4/2015 |

\* cited by examiner

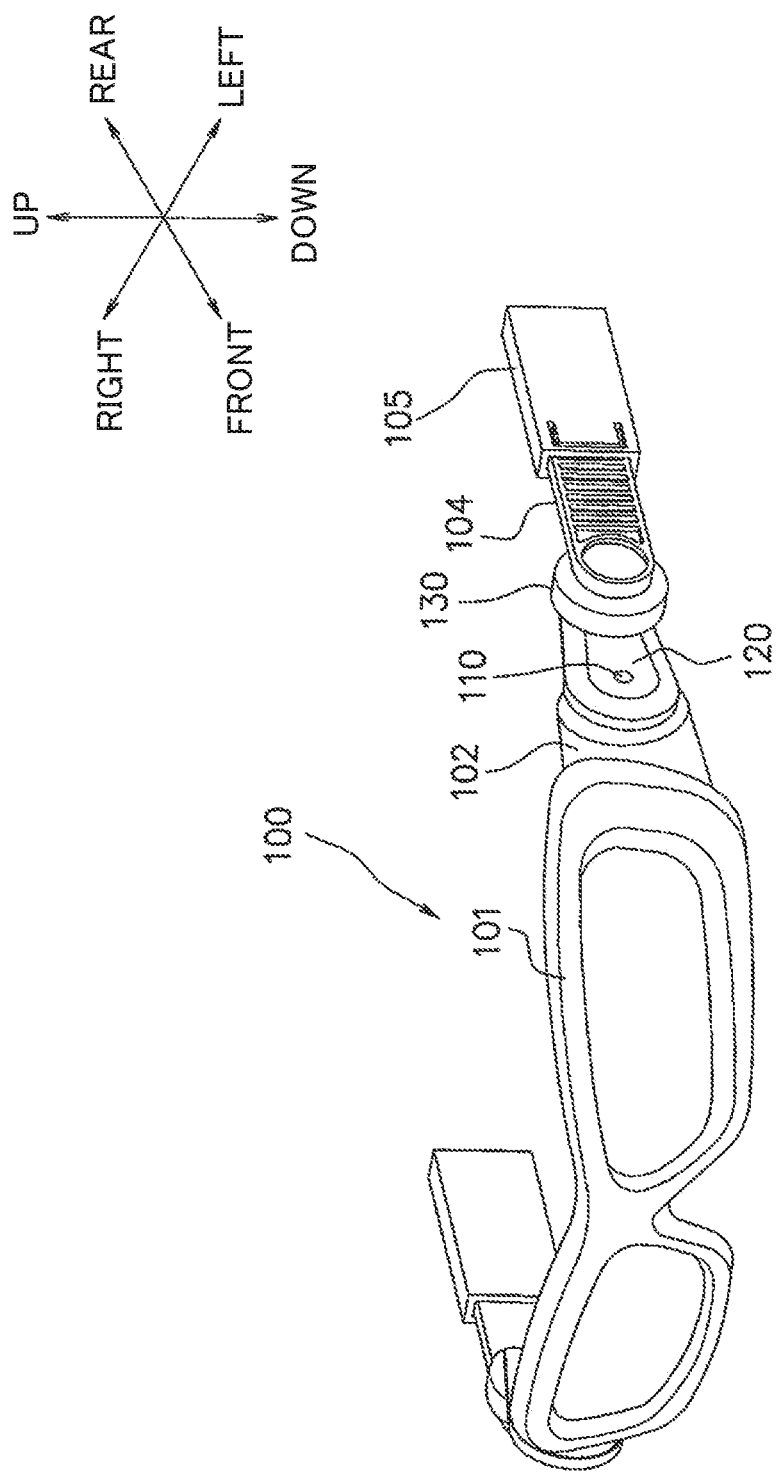

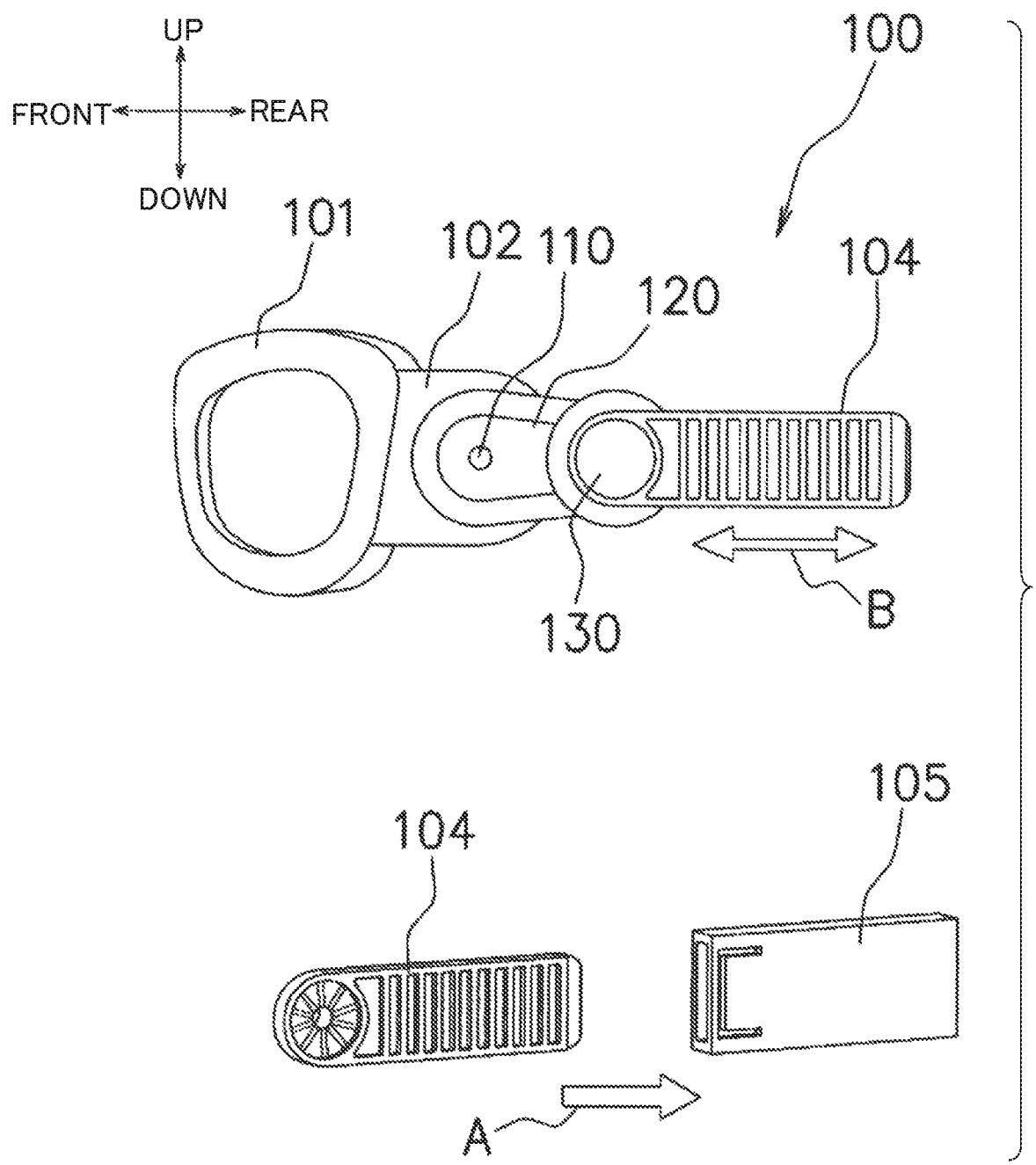

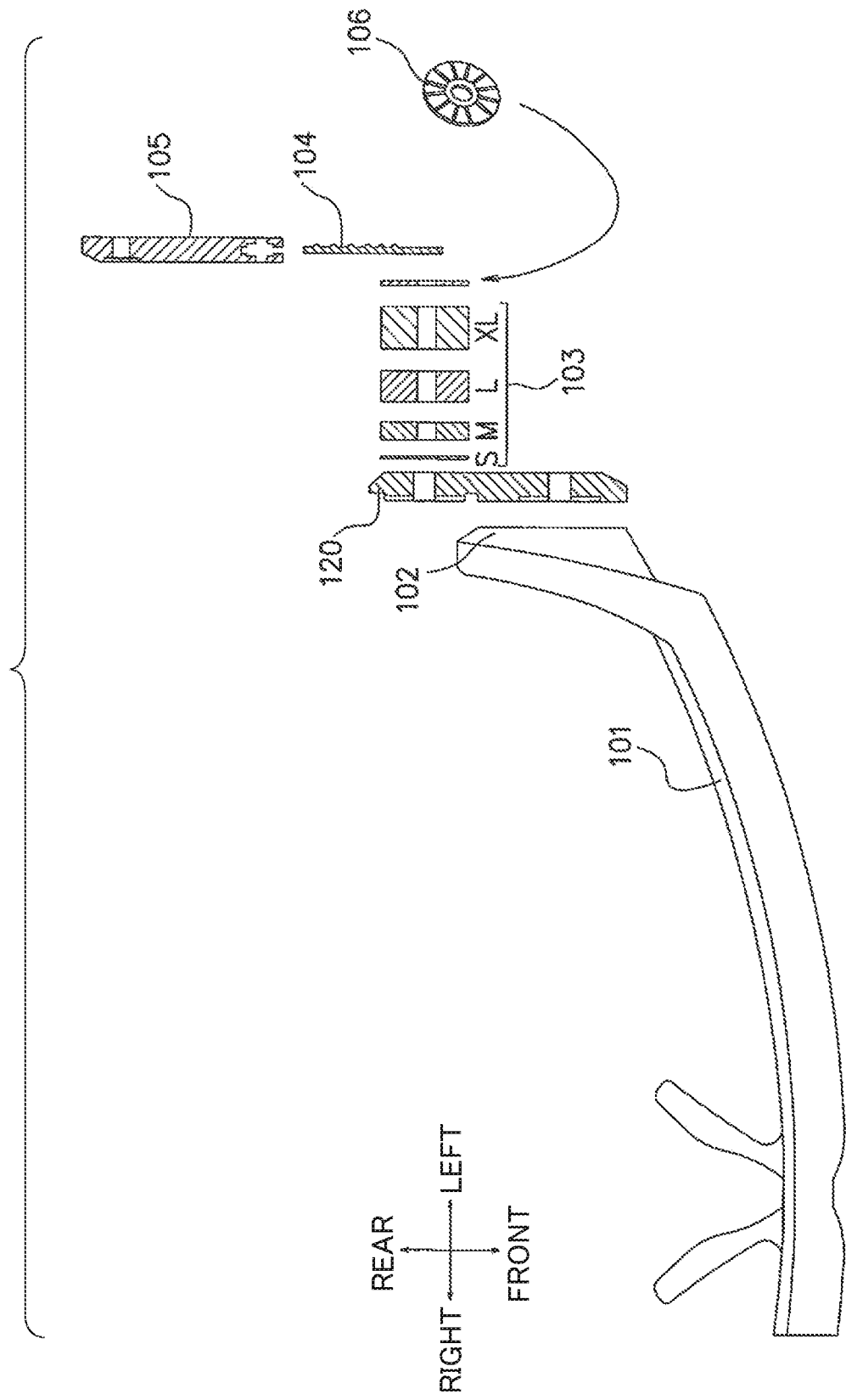

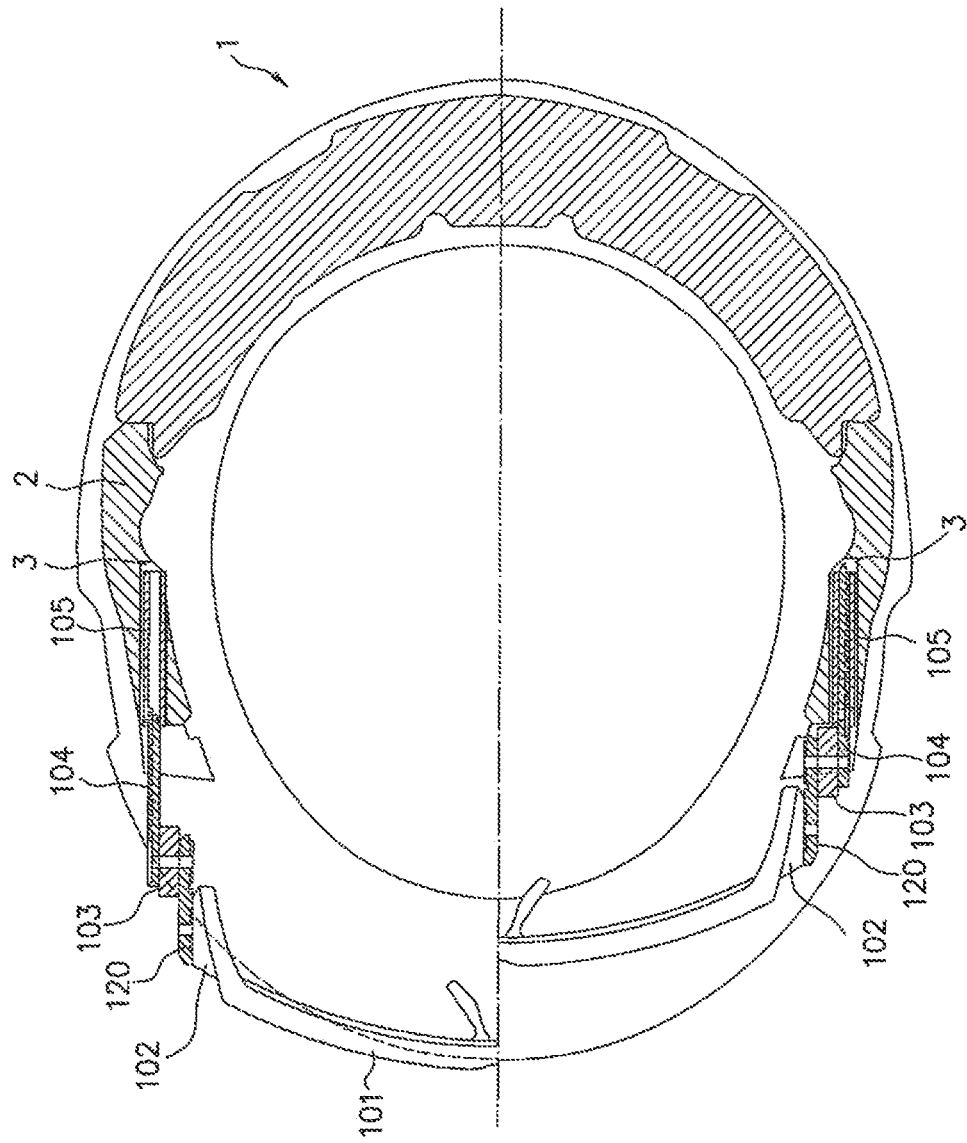

LENS UNIT ATTACHMENT MECHANISM

TECHNICAL FIELD

The present invention relates to a lens unit attachment mechanism for spectacles, sunglasses, or the like.

BACKGROUND ART

The present invention relates to a lens unit attachment mechanism to attach a component including lenses (a lens unit) of spectacles, sunglasses, or the like to a helmet.

Hitherto, a spectacle, such as widely used sunglasses, has been configured by lenses and a spectacle frame (outer frame) to support the lenses when it is worn. A spectacle frame (outer frame) is configured by two rims (casings) which hold both lenses, and two temples which are connected rotationally to the rims (casings) via hinges with a predetermined length at a predetermined angle. There is a need to prepare the spectacle frames (outer frames) in various sizes or, offer a service designed to adjust them in order to fit for the faces of wearers that have various shapes and sizes (for example the length and width of the face, and the distance from the eyes to the ears).

U.S. Pat. No. 4,544,245 discloses a spectacle frame in which the length of the temples and the angle of the lenses can be adjusted within a predetermined range in order to eliminate the troublesome task of selecting or adjusting such spectacle frames (outer frames).

International Publication (WO) No. 2015/059014 discloses a mechanism with an object of securing a field of view through protective glasses by adapting to the length of the face and the positions of the eyes of a wearer, and providing a good fitting sensation through fine adjustments of the position and angle of the protective glasses using one free hand while the wearer is performing a task. Projection portions provided at side faces of the protective glasses and recesses provided at spectacle support arms coupled to the protective glasses are engaged in stages to adjust the angles between the protective glasses and the spectacle support arms, and the spectacle support arms fit snugly into and slide through length direction slits provided at brackets to adjust the distance between the safety spectacles and the spectacle support arms.

Japanese Patent Application Laid-Open (JP-A) No. 2000-178820 discloses a helmet with an object of allowing a spectacle frame to pass through easily when a motorcycle rider puts on spectacles after putting on the helmet, even when ear cups are in close contact with the temples of the rider, and also of eliminating a sense of discomfort caused by pressing on the spectacle frame after putting on the spectacles. The ear cups are provided with spectacle frame passage recesses through which the spectacle frame is passed when the motorcycle rider puts on the spectacles after putting on the helmet.

Japanese Utility Model Application Laid-Open (JP-U) No. H04-127221 discloses a helmet with an object of avoiding frustration when handling spectacles when a spectacle wearer puts on or takes off the helmet. An inner body of the helmet is provided with a retention means that retains temple portions of the spectacles in a substantially horizontal state such that the spectacles can be put on or taken off.

SUMMARY OF INVENTION

Technical Problem

In the mechanism described in U.S. Pat. No. 4,544,245, the angle of the lens is changed about a radius of rotation corresponding to the width of the temples, and the temples are partially extendable. In WO No. 2015/059014, the recess provided at one end side of each spectacle support arm so as to change an angle in an up-down direction of the safety spectacles and the projection portion provided at each end of the protective glasses engage in increments at a predetermined angle, and the spectacle support arms slide along grooves provided along the length direction of the brackets to enable the length of the spectacle support arms to be adjusted. In the inventions described in these documents, the angles of the lenses or protective glasses can only be adjusted in approximate increments, and only within a limited range. Moreover, since it is necessary to retain the lenses or protective glasses securely, the distance between the lenses or protective glasses and the wearer is likewise only adjustable within a limited range.

In the helmet described in JP-A No. 2000-178820, although it is easier to put on the spectacles after putting on the helmet, it is not possible to adjust the angle of the spectacles or the length of the frame. Moreover, in the helmet described in JP-U No. H04-127221, although the spectacles retained by the retention means can be set to an appropriate state by moving the spectacles in a front-rear direction, it is not possible to adjust the angle in an up-down direction.

In consideration of the above circumstances in the background art, the present invention is to provide a lens unit attachment mechanism that secures a field of view of a helmet wearer by adapting lenses according to the various face lengths and eye positions of helmet wearers, and that enables a good fitting sensation to be obtained by performing fine adjustment of the position and angle of the lenses.

Solution to Problem

In order to resolve the above issues, a first embodiment of a lens unit attachment mechanism is the mechanism for attaching a lens unit so as to retain the lens unit in front of eyes of a helmet wearer. The lens unit attachment mechanism includes a lens unit configured by a frame member to support a pair of lenses and side frame members extending rearward of the lenses from left and right end portions of the frame member, angle adjustment members that are respectively coupled to the side frame members and that adjust angles of elevation and depression of the lens unit, a first member that axially supports such that each of the side frame members and each of the angle adjustment members are able to pivot with respect to each other, position adjustment members that adjust a horizontal direction position of the lens unit, a second member that axially supports such that each of the angle adjustment members and each of the position adjustment members are able to pivot with respect to each other, and position adjustment retention members that respectively retain helmet-side end portions of the position adjustment members so as to enable the position adjustment members to extend and retract in the horizontal direction.

A second embodiment of a lens unit attachment mechanism is the first embodiment, further including a size adjustment member that is inserted between a first face of the side frame member and a face opposing the first face, which is oriented substantially parallel to the horizontal direction of the position adjustment members, and/or that is inserted between a second face of the angle adjustment member and a face opposing the second face, which is oriented substantially parallel to the horizontal direction of the position adjustment members, so that the lens unit is adapted to be adjusted to a left-right direction width of a face of the helmet wearer by the size adjustment member.

A third embodiment of a lens unit attachment mechanism is the second embodiment further including an angle retention member that is inserted between said first face and the face opposing said first face, and/or between said second face and the face opposing said second face, so that the angle retention member retains an angle formed between the side frame member and the angle adjustment member, and/or an angle formed between the angle adjustment member and the position adjustment member as viewed along the left-right direction of a wearer's face.

A fourth embodiment of a lens unit attachment mechanism is any one of the first to the third embodiment, wherein the lens unit is a video display device.

Advantageous Effects of Invention

The lens unit attachment mechanism according to the present invention enables to secures a field of view of a helmet wearer by adapting a lens unit according to the various face lengths and eye positions of wearers, and obtain a good fitting sensation by performing fine adjustment of the position and angle of the lens unit.

BRIEF DESCRIPTION OF DRAWINGS

FIG. 1 is a perspective view illustrating an overall lens unit and its attachment mechanism according to an exemplary embodiment.

FIG. 2A is a side view from the left, illustrating relevant portions of a lens unit and its attachment mechanism according to an exemplary embodiment.

FIG. 4 is a plan view illustrating an example in which a size adjustment washer and a washer with an anti-slip function and an angle adjustment function are attached to a lens unit and its attachment mechanism according to an exemplary embodiment.

FIG. 6 is a cross-section taken along A-A in FIG. 5, in which a lens unit and its attachment mechanism according to an exemplary embodiment are mounted to a helmet.

DESCRIPTION OF EMBODIMENTS

Figure 2B:
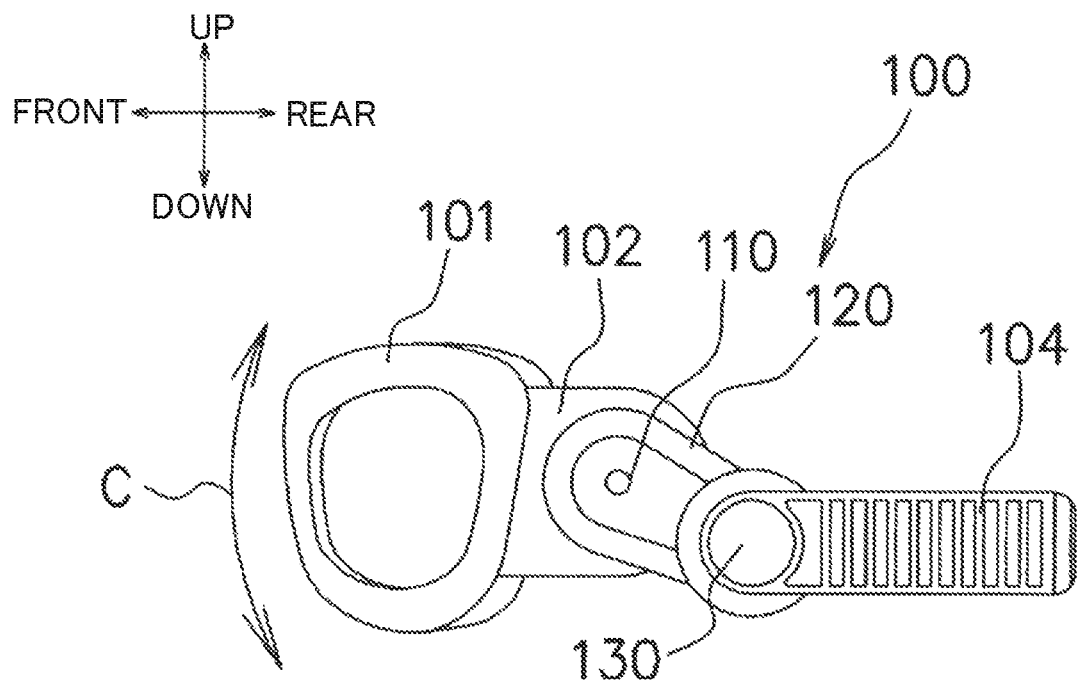
FIG. 2B is a side view from the left, illustrating relevant portions of a lens unit and its attachment mechanism according to an exemplary embodiment to explain a case in which a second member is used to adjust an up-down direction position of a lens unit.

The present invention relates to a lens unit attachment mechanism for attaching a lens unit in front of the eyes of a helmet wearer. Specifically, either face of side frame members 102 is substantially parallel to the front-rear direction on side frame members 102, that extend rearward from left and right direction terminal portions (also referred to as left and right end portions) of a frame member 101, which supports a pair of lenses of a lens unit 100. A face opposing said either face is substantially parallel to the front-rear direction at one end side of an angle adjustment arm 120, which serves as an example of an angle adjustment member that adjusts the angles of elevation and depression of the lenses. Both faces are superimposed on each other, and a first member 110 axially supports the side frame member 102 and the corresponding angle adjustment arm 120 so as to allow pivoting with respect to each other as viewed along the left-right direction. This thereby enables an angle in the up-down direction of the lens unit to be adjusted.

Moreover, either face is substantially parallel to the front-rear direction at another end side of angle adjustment arms 120. A face opposing said either face is substantially parallel to the front-rear direction at one end side of a ratchet stay 104, which serves as an example of a position adjustment member that adjusts a position in the front-rear direction (horizontal direction) of the lenses. Both faces are superimposed on each other, and a second member 130 axially supports the angle adjustment arm 120 and the ratchet stay 104 so as to allow pivoting with respect to each other as viewed along the left-right direction. This thereby enables a position in the up-down direction of the lens unit to be adjusted.

A ratchet stay holder 105, serving as an example of a position adjustment retention member that retains another end side, namely, a helmet-side end portion, of the ratchet stay 104 so as to allow extending and retracting in the front-rear direction, is also included. This enables a front-rear direction position of the lens unit to be adjusted. In this manner, the lenses are adapted to the various face lengths and eye positions of helmet wearers so as to secure the field of view of the wearer. Moreover, a good fitting sensation can be obtained by performing fine adjustment of the position and angle of the lens unit.

In the following explanation, a gaze-forward direction of the wearer when the helmet is attached the lens unit 100 is defined as the front, and the opposite direction thereto is defined as the rear. The left and right are defined as one direction and the opposite direction thereto out of lateral directions lying in the same plane as the gaze of the wearer. Upward and downward are defined as one direction and the opposite direction thereto out of directions orthogonal to the same plane as the front-rear and left-right directions.

First, explanation follows regarding the overall lens unit and its attachment mechanism according to the present exemplary embodiment. FIG. 1 is a perspective view illustrating the overall lens unit and its attachment mechanism according to the present exemplary embodiment. In FIG. 1, the lens unit 100 according to the present exemplary embodiment includes the frame member 101 to support the lenses, and the side frame members 102 that each extend rearward, orthogonally to the left-right direction, from a left-right direction end portion of the frame member 101. The lens unit 100 further includes the angle adjustment arms 120 that each have the one end side axially supported together with the corresponding side frame member 102 by the first member 110, the ratchet stays 104 that each have the one end side axially supported together with the other end side of the corresponding angle adjustment arm 120 by the second member 130, and the ratchet stay holders 105 that each support the corresponding ratchet stay 104 so as to allow extension and retraction in the front-rear direction of the face of the helmet wearer. Each ratchet stay holder 105 is, for example, formed with a recess into which the corresponding ratchet stay 104 is inserted so as to be capable of extending and retracting.

Adjustment of the angle of the lens unit 100 in the up-down direction of the face (the angles of elevation and depression of the lens) can be performed by tilting the lens unit 100 in the up-down direction of the face about the axis of the first member 110, by tilting the lens unit 100 in the up-down direction of the face about the axis of the second member 130, or by tilting the lens unit 100 in the up-down direction of the face about the axis of the first member 110 and the axis of the second member 130. Adjustment of the position of the lens unit 100 in the up-down direction of the face is achieved by moving the lens unit 100 in the up-down direction of the face about the axis of the second member 130, and then adjusting the angle about the axis of the first member 110. Moreover, adjustment of the position of the lens unit 100 in the front-rear direction of the face can be performed by inserting each ratchet stay 104 into the corresponding ratchet stay holder 105 or pulling the ratchet stay 104 out from the ratchet stay holder 105. Note that in FIG. 1, explanation is given regarding the left side face of the lens unit 100. However, the right side face is configured similarly to the left side face.

FIG. 1 illustrates a specific example in which a left-right direction outer side face of the side frame member 102 and a left-right direction inner side face at the one end side of the angle adjustment arm 120 are superimposed on each other, and a left-right direction outer side face at the other end side of the angle adjustment arm 120 and a left-right direction inner side face at the one end side of the ratchet stay 104 are superimposed on each other. However, obviously either face of the side frame member 102 and either face of the angle adjustment arm 120 may be superimposed on each other, and either face of the angle adjustment arm 120 and either face of the ratchet stay 104 may be superimposed on each other, as desired.

Next, explanation follows regarding relevant portions of the lens unit and its attachment mechanism according to the present exemplary embodiment in a case in which the up-down direction position of the lens unit is adjusted using the second member as a relevant portion, and a case in which the up-down direction angle of the lens unit is adjusted using the first member as a relevant portion.

Figure 2C:
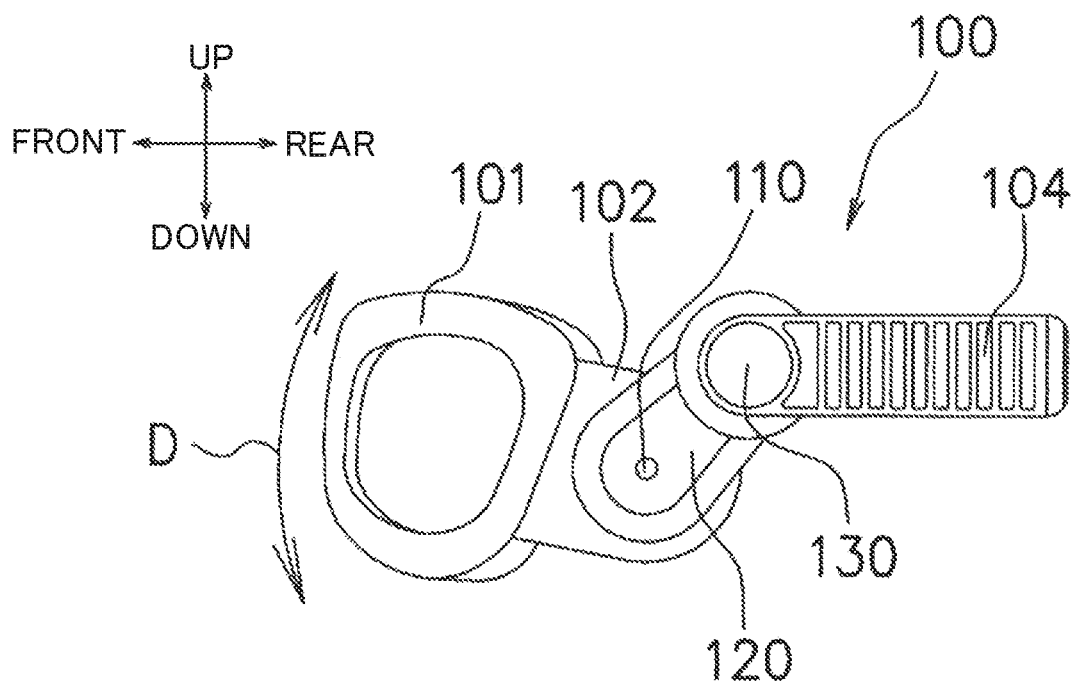
FIG. 2C is a side view from the left, illustrating relevant portions of a lens unit and its attachment mechanism according to an exemplary embodiment to explain a case in which a first member is used to adjust an up-down direction angle of a lens unit.

FIG. 2A is a side view from the left, illustrating relevant portions of the lens unit and its attachment mechanism according to the present exemplary embodiment. FIG. 2B is a side view from the left, illustrating relevant portions of the lens unit and its attachment mechanism according to the present exemplary embodiment, and is an explanatory diagram for a case in which the up-down direction position of the lens unit is adjusted using the second member. FIG. 2C is a side view from the left, illustrating relevant portions of the lens unit and its attachment mechanism according to the present exemplary embodiment, and is an explanatory diagram for a case in which the up-down direction angle of the lens unit is adjusted using the first member.

As illustrated in FIG. 2A, the side frame member 102 and the one end side of the angle adjustment arm 120 are axially supported by the first member 110 such that the side frame member 102 and the angle adjustment arm 120 pivot with respect to each other as viewed along the left-right direction. The other end side of the angle adjustment arm 120 and the one end side of the ratchet stay 104 are axially supported by the second member 130 such that the angle adjustment arm 120 and the ratchet stay 104 pivot with respect to each other as viewed along the left-right direction. The ratchet stay 104 is inserted into the ratchet stay holder 105, formed in a hollow shape, for example, in the direction of the arrow A in FIG. 2A. The ratchet stay 104 is configured so as to be capable of extending and retracting in both directions with respect to the ratchet stay holder 105, as indicated by the bidirectional arrow B.

In FIG. 2B, the angle adjustment arm 120 is inclined in the upward direction with respect to the face of the wearer around the second member 130, such that the lens unit 100 coupled to the one end side of the angle adjustment arm 120 is moved to an upward direction position of the face. Note that positional movement in the downward direction of the face is also possible, as indicated by the bidirectional arrow C.

In FIG. 2C, the angle adjustment arm 120 is inclined in the downward direction with respect to the face around the second member 130, and the lens unit 100 is inclined in the upward direction of the face about the first member 110, such that the lens unit 100 approaches the face, and the angle thereof is adjusted in the upward direction. Note that the angle may also be adjusted in the downward direction of the face, as indicated by the bidirectional arrow D.

Although not illustrated in the drawings, the angle adjustment arm 120 can be inclined around the second member 130 to move the lens unit 100 in the up-down direction of the face while the side frame member 102 of the lens unit 100 and the angle adjustment arm 120 are maintained in a parallel state. Moreover, FIG. 2A to FIG. 2C illustrate the left side face of the lens unit 100. However, the right side face is configured similarly to the left side face.

Figure 3A:
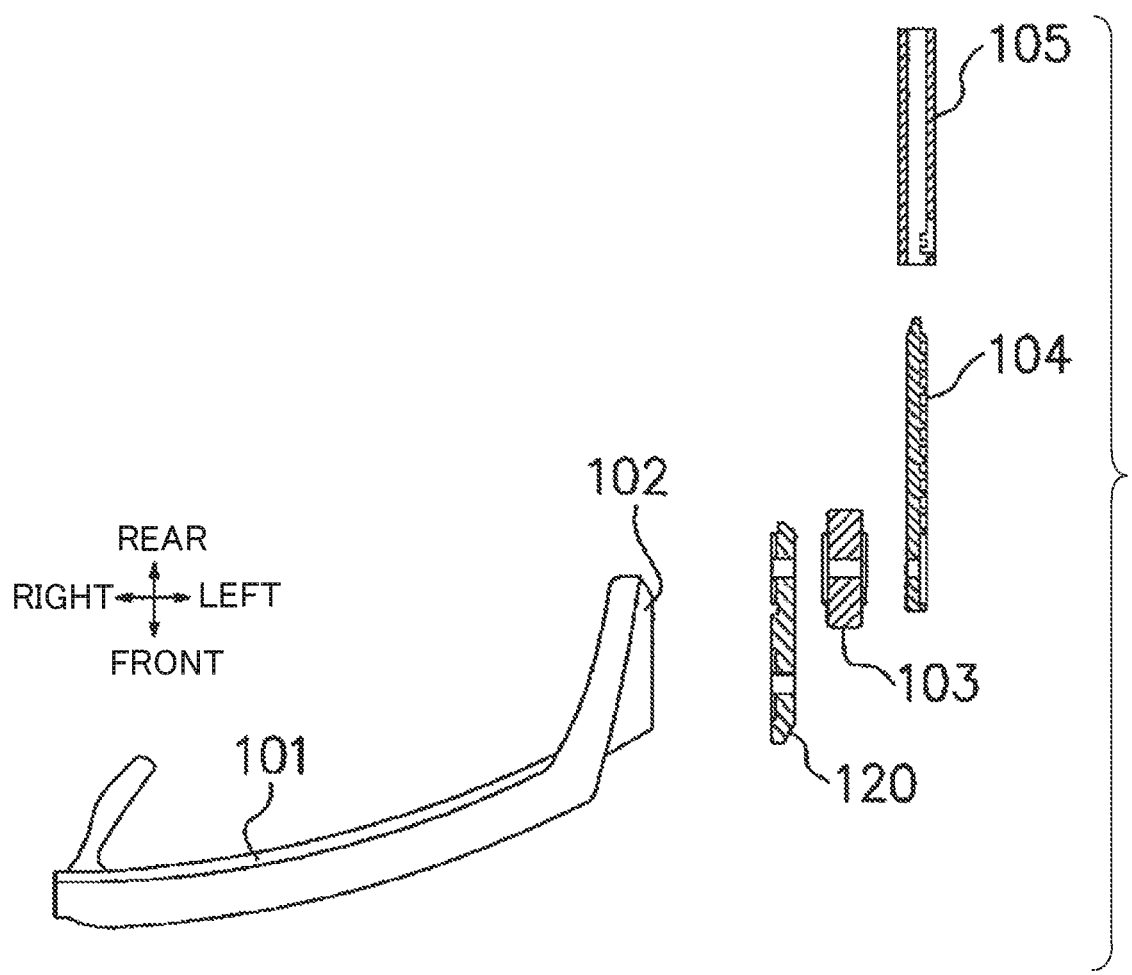
FIG. 3A is a plan view illustrating relevant portions of a lens unit and its attachment mechanism according to an exemplary embodiment.

Next, explanation follows regarding relevant portions of the lens unit and its attachment mechanism according to the present exemplary embodiment. FIG. 3A is a plan view illustrating relevant portions of the lens unit and its attachment mechanism according to the present exemplary embodiment, FIG. 3B is a front view illustrating relevant portions of the lens unit and its attachment mechanism according to the present exemplary embodiment, and FIG. 3C is a side view from the left illustrating relevant portions of the lens unit and its attachment mechanism according to the present exemplary embodiment.

Figure 3B:
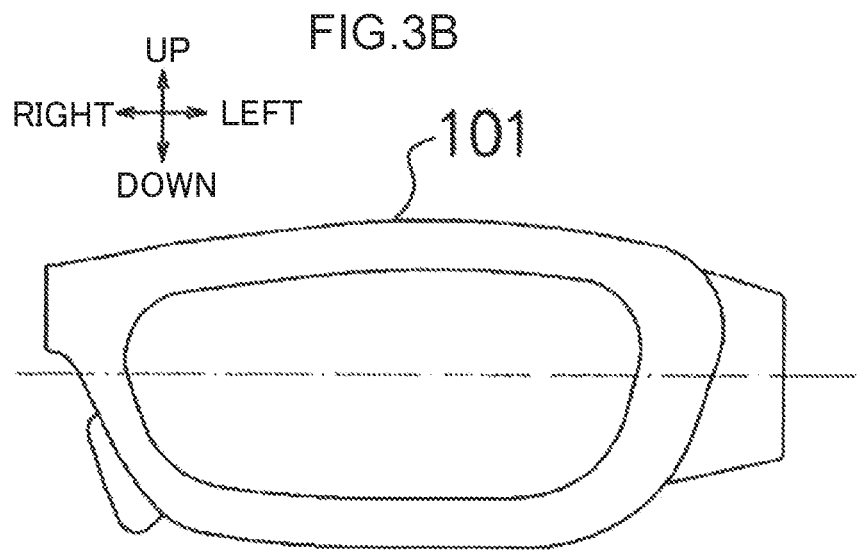
FIG. 3B is a front view illustrating relevant portions of a lens unit and its attachment mechanism according to an exemplary embodiment.
Figure 3C:
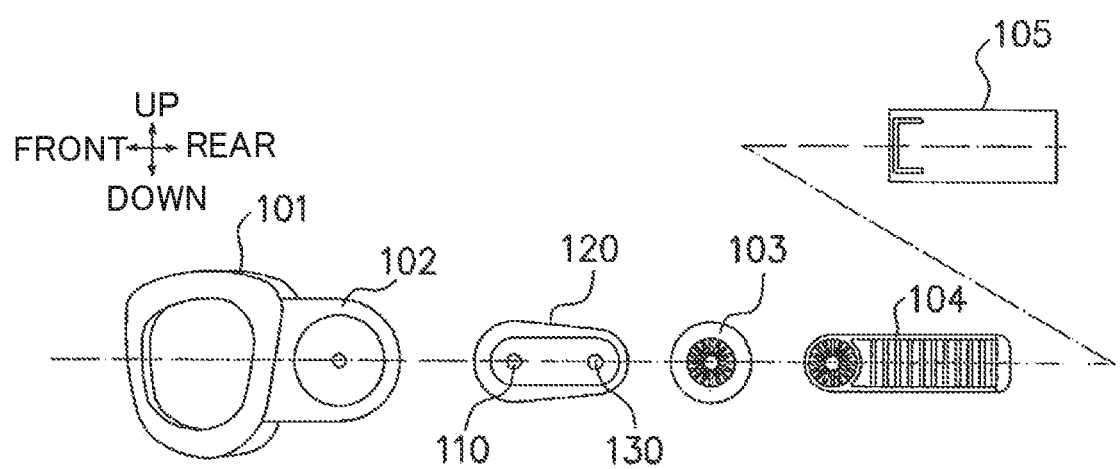
FIG. 3C is a side view from the left, illustrating relevant portions of a lens unit and its attachment mechanism according to an exemplary embodiment.

As illustrated in FIG. 3A, FIG. 3B, and FIG. 3C, the side frame member 102 on the left side of the lens unit 100 and the one end side of the angle adjustment arm 120 are coupled together. The other end side of the angle adjustment arm 120 and the one end side of the ratchet stay 104 are coupled together through a size adjustment washer 103, serving as an example of a size adjustment member. The other end side of the ratchet stay 104 is inserted into the hollow ratchet stay holder 105.

As described later, the size adjustment washer 103 adjusts the distance between the side frame member 102 and the ratchet stay 104 according to a lateral width size of the face of the wearer wearing the lens unit 100. FIG. 3A, FIG. 3B, and FIG. 3C illustrate an example in which the size adjustment washer 103 is inserted between the angle adjustment arm 120 and the ratchet stay 104. However, the size adjustment washer 103 may be inserted between the side frame member 102 and the angle adjustment arm 120, or may be inserted both between the side frame member 102 and the angle adjustment arm 120 and between the angle adjustment arm 120 and the ratchet stay 104. FIG. 3A, FIG. 3B, FIG. 3C illustrate the left side face of the lens unit 100. However, the right side face is configured similarly to the left side face.

Next, explanation follows regarding an example of attachment of the size adjustment member and an example of attachment of an angle retention member to the lens unit and its attachment mechanism according to the present exemplary embodiment. FIG. 4 is a plan view illustrating an example of attachment of size adjustment washers, serving as examples of the size adjustment member, and an example of attachment of a washer with an anti-slip function and an angle adjustment function, and serving as an example of the angle retention member, in the lens unit and its attachment mechanism according to the present exemplary embodiment.

First, explanation follows regarding a method for adjusting the distance between the side frame member 102 and the ratchet stay 104 according to the lateral width size of the face of the wearer wearing the lens unit 100. In FIG. 4, the other end side of the angle adjustment arm 120 and the one end side of the ratchet stay 104 are coupled together through the size adjustment washer 103. The size adjustment washer 103 has a function of adjusting the distance between the side frame member 102 and the ratchet stay 104 according to the lateral width size of the face of a person wearing the lens unit 100. FIG. 4 illustrates examples of an S size, an M size, an L size, and an XL size corresponding to lateral width sizes of the face of the wearer of the lens unit 100. Obviously, however, there is no limitation to these sizes.

As illustrated in FIG. 4, in addition to a function to adjust the angle of the lens unit 100 in the up-down direction of the face of the wearer, the angle adjustment arm 120 may also be provided with a washer 106, serving as an example of an angle retention member with an anti-slip function for maintaining a specific angle after the angle of the lens unit adjusted. This enables the lens units 100 to use in various fields in which precision in the position (angle) of the lens unit 100 is demanded.

Note that FIG. 4 illustrates an example in which the washer 106 with an anti-slip function is inserted between the angle adjustment arm 120 and the ratchet stay 104. However, the washer 106 with an anti-slip function may be inserted between the side frame member 102 and the angle adjustment arm 120, or may be inserted both between the side frame member 102 and the angle adjustment arm 120 and between the angle adjustment arm 120 and the ratchet stay 104. Moreover, FIG. 4 illustrates the left side face of the lens unit 100. However, the right side face is configured similarly to the left side face.

Figure 5:
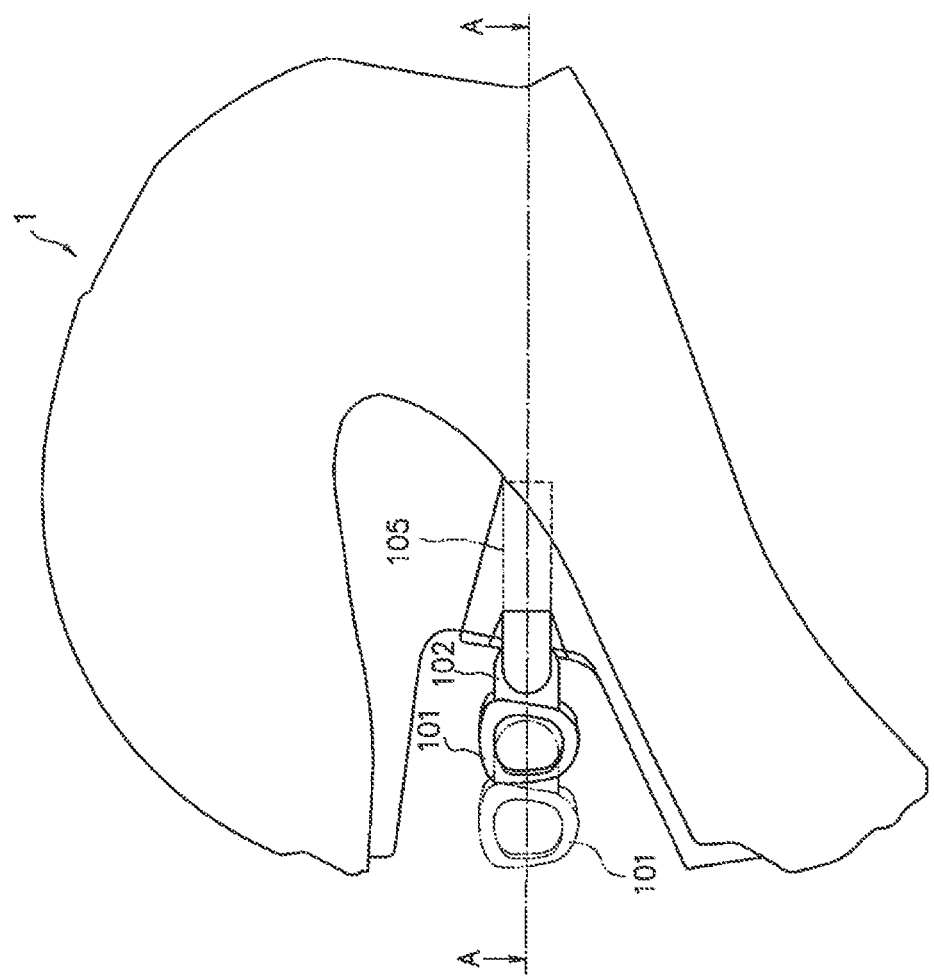
FIG. 5 is a side view from the left, illustrating an example in which a lens unit and its attachment mechanism according to an exemplary embodiment are mounted to a helmet.

Next, explanation follows regarding a case in which the lens unit and its attachment mechanism according to the present exemplary embodiment are mounted to a helmet. FIG. 5 is a side view from the left illustrating an example in which the lens unit and its attachment mechanism according to the present exemplary embodiment are mounted to a helmet. FIG. 6 is a cross-section taken along A-A in FIG. 5 when the lens unit and its attachment mechanism according to the present exemplary embodiment are mounted to a helmet.

As illustrated in FIG. 5 and FIG. 6, each ratchet stay holder 105 is attached to a recess 3 formed at a location close to the head of the wearer at an inner side of a helmet 1. FIG. 6 illustrates an example in which the ratchet stay holders 105 are mounted in recesses 3 formed in a mask liner 2 fixed to the inner side of the helmet 1. Obviously the recesses 3 may be provided to any location fixed to the inner side of the helmet.

As described above, in the present exemplary embodiment the angle formed between the side frame member 102 and the angle adjustment arm 120, and the angle formed between the angle adjustment arm 120 and the ratchet stay 104, are changed to enable the position of the lens unit 100 to be adjusted over a wide range. In short, the position and incline of the lens unit 100 in the up-down direction can be varied by using the fulcrum points axially supported at plural locations. Accordingly, the advantageous effect of being able to adjust the position of the lens unit 100 precisely and flexibly so as to better fit the wearer can be obtained, unlike in the related technology.

Moreover, when an angle that fits the wearer has been chosen, since the washer with an anti-slip function is attached to maintain the angle, the state fitting the wearer can be maintained for a long time.

Accordingly, competitive racers using two-wheeled vehicles such as bicycles and motorbikes, F1 racing drivers, and the like are able to focus on their race due to being able to maintain a good fitting sensation that is almost unaffected by sweat, vibration, and the like by wearing the lens unit, that is equipped with the lens unit attachment mechanism of the present invention, when wearing a helmet.

The present invention may also be applied to technology in which various information, such as numerical data on meters required for driving or information relating to a field of view to the rear, is displayed in a predetermined region of a lens of spectacles worn by a rider wearing a helmet. In other words, the lens unit is employed as a video display device. Such information needs to be suitably displayed in a visible position, such that it does not obstruct the field of view of the driver when driving. Therefore, slippage of the position of the spectacles during driving could have serious safety implications.

Under such conditions, the lens unit and its attachment mechanism of the present invention are provided to a rider wearing a helmet, such that the lens unit is adjusted to the position (angle) that best fits the rider. Accordingly, slippage of the lens unit during driving does not occur. Accordingly, various information can be displayed at an appropriate position on the lens unit, and the field of view of the rider can be well secured, enabling the advantageous effect of adequately securing safety to be obtained.

As described above, the present invention relates to an attachment mechanism to attach a lens unit to a helmet. Specifically, the side frame member 102 extending rearward from the left-right direction end portion of the frame member 101, which supports the lenses of the lens unit 100, has one face running substantially parallel to the front-rear direction. The one face and the opposing face, running substantially parallel to the front-rear direction at the one end side of the angle adjustment arm 120, which adjusts the angles of elevation and depression of the lenses, are superimposed on each other. As viewed along the left-right direction, the first member 110 axially supports the side frame member 102 and the angle adjustment arm 120 so as to allow pivoting with respect to each other.

Moreover, the angle adjustment arm 120 has one face running substantially parallel to the front-rear direction at the other end side of the angle adjustment arm 120. The one face and the opposing face, running substantially parallel to the front-rear direction at the one end side of the ratchet stay 104 that adjusts the front-rear direction position of the lenses, are superimposed on each other. As viewed along the left-right direction, the second member 130 axially supports the angle adjustment arm 120 and the ratchet stay 104 so as to allow pivoting with respect to each other.

The ratchet stay holder 105 that retains the other end side of the ratchet stay 104 so as to allow extending and retracting in the front-rear direction is also included. A lens unit attachment mechanism is thereby obtained that is capable of securing the field of view of spectacles by adapting to the length of the face and positions of the eyes of various spectacle wearers, and is also capable of obtaining a good fitting sensation of the spectacles by performing fine adjustment of positions and angles.

Explanation has been given regarding an exemplary embodiment of the present invention; however, exemplary embodiments of the present invention are not limited to the exemplary embodiment described above. Namely, various modifications, including other exemplary embodiments, additions, changes, and omissions that might be conceived by a practitioner skilled in the art may be implemented within the scope of the present invention, and such modifications are included in the scope of the present invention as long as the operation and advantageous effects of any aspect are exhibited.

The invention claimed is:

1. A lens unit attachment mechanism for attaching a lens unit so as to retain the lens unit in front of eyes of a helmet wearer, the lens unit attachment mechanism comprising:
   a lens unit configured by a frame member to support a pair of lenses and side frame members extending rearward of the lenses from left and right end portions of the frame member;
   angle adjustment members respectively coupled to the side frame members and adjusting angles of elevation and depression of the lens unit;
   a first member axially supporting such that each of the side frame members and each of the angle adjustment members are able to pivot with respect to each other;
   position adjustment members adjusting a horizontal direction position of the lens unit;
   a second member axially supporting such that each of the angle adjustment members and each of the position adjustment members are able to pivot with respect to each other; and
   position adjustment retention members respectively retaining helmet-side end portions of the position adjustment members so as to enable the position adjustment members to extend and retract in the horizontal direction,
   wherein the lens unit attachment mechanism further comprises a size adjustment member that is inserted between a first face oriented substantially parallel to the horizontal direction of one of the side frame members and a face opposing the first face, inserted between a second face oriented substantially parallel to the horizontal direction of one of the angle adjustment members and a face opposing the second face, or a combination thereof, such that the lens unit is adapted to be adjusted to a left-right direction width of a face of the helmet wearer.

2. The lens unit attachment mechanism of claim 1, further comprising an angle retention member that is inserted between the first face of the one of the side frame members and the face opposing the first face, inserted between the second face of the one of the angle adjustment members and the face opposing the second face, or a combination thereof,
   wherein the angle retention member retains an angle formed between the one of the side frame members and the one of the angle adjustment members as viewed along the left-right direction, retains an angle formed between the one of the angle adjustment members and one of the position adjustment members as viewed along the left-right direction, or a combination thereof.

3. The lens unit attachment mechanism of claim 1, wherein the lens unit is a video display device.

4. The lens unit attachment mechanism of claim 2, wherein the lens unit is a video display device.

* * * * *